United States Patent [19]

Warriner

[11] Plant 5,244

[45] Jun. 12, 1984

[54] ROSE PLANT 'JACRUS 77-3372'

[75] Inventor: William A. Warriner, Tustin, Calif.

[73] Assignee: Jackson & Perkins Company, Medford, Oreg.

[21] Appl. No.: 404,601

[22] Filed: Aug. 2, 1982

[51] Int. Cl.[3] ..... A01H 5/00

[52] U.S. Cl. ..... Plt./24

[58] Field of Search ..... Plt./24

*Primary Examiner*—James R. Feyrer

*Attorney, Agent, or Firm*—Klarquist, Sparkman, Campbell, Leigh & Whinston

[57] ABSTRACT

A new variety of rose plant which remains clear yellow, with reddish-purple styles and fewer side buds under the terminal flowers as compared to its parent Golden Times.

1 Drawing Figure

1

This present invention relates to a new and distinct variety of rose plant of the floribunda class which was originated by me by crossing an unnamed variety, with the variety Golden Times, U.S. Plant Pat. No. 4,044.

The primary objective of this breeding was to produce a new rose variety combining the keeping quality and plant habit of Golden Times with other characteristics of the seed parent. This objective was substantially achieved along with other desirable improvements as evidenced by the following unique combination of characteristics which are outstanding in the new variety and which distinguish it from its parents, as well as from all other varieties of which I am aware:

1. Color is very slightly lighter than Golden Times.
2. Color of this new variety remains clear yellow, while petals of Golden Times often display reddish tints near the edges.
3. Receptacles of the new variety are larger than those of Golden Times.
4. Color of styles is a reddish purple on the new variety compared to pink styles of Golden Times.
5. Plant habit and foliage of the new variety is similar to that of Golden Times, except that fewer side buds are produced under the terminal flowers on the new variety.

Asexual reproduction of this new variety by budding, as performed at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color in terminology in accordance with The Royal Horticultural Society Colour Chart except where ordinary dictionary significance of color is indicated.

Parentage:

*Seed parent.*—Unnamed variety.

*Pollen parent.*—Golden Times, U.S. Plant Pat. No. 4,044.

Classification:

*Botanical.*—Rosa hybrid.

*Commercial.*—Floribunda.

2

FLOWER

Observations made from specimens grown in greenhouse at Irvine, Calif. in April.

Blooming habit: Continuous.

Bud:

*Size.*—One inch when petals start to unfurl.

*Form.*—Short, blunt top.

*Color.*—When sepals first divide, yellow 15C; when half blown; upper side of petals, yellow 15C; lower side of petals, yellow 15C.

*Sepals.*—Color: Outer surface, green 138B. Three appendaged sepals normally appendaged. Two unappendaged sepals hairy edged, with some stipitate glands.

*Receptacle.*—Color: Green 138B. Shape: Apple. Size: Very large. Surface: Smooth.

*Peduncle.*—Length: Medium. Surface: Prickly and glandular. Color: Light green. Strength: Stiff, erect and heavy.

*Opening.*—Petals curl under, appear pointed.

Bloom:

*Size.*—Medium. Average open size, 3½".

*Borne.*—Singly, few in clusters.

*Stems.*—Long, medium, strong.

*Form.*—High center. Permanence: Retains its form to the end. Outer petal edges slightly curled.

*Petalage.*—Number of petals under normal conditions 45-50.

*Color.*—Center of flower: Upper side of petals, yellow 15C; reverse side of petals, yellow 15C; base of petals, yellow 15C; general tonality from a distance, yellow 15C.

*Variegations.*—None.

*Discoloration.*—General tonality at end of first day, yellow 15C. Third day, yellow 15D.

*Fragrance.*—Strong.

Petals:

*Texture.*—Thick, quite stiff.

*Shape.*—Round.

*Form.*—Moderately quilled.

*Arrangement.*—Imbricated (regularly arranged shingle-like). Petaloids in center, few.

*Persistence.*—Drop off cleanly.

*Lastingness.*—On the plant, very long. As cut flower, very long.

Reproductive parts:

*Anthers.*—Medium. Color, yellow. Arrangement, regular around styles.

*Filaments.*—Color, yellow.
*Pollen.*—Gold yellow.
*Styles.*—Color, red purple 57B.
*Stigmas.*—Color, white.

PLANT

Form: Bush.
Growth: Very vigorous, upright, branching.
Foliage: Number of leaflets on normal mid-stem leaves, 5 or 7.
*Size.*—Large.
*Quantity.*—Normal.
Color.—New foliage, green 138B overlaid with red purple 59B. Old foliage, green 136B.
Leaflets:
*Shape.*—Oval pointed.
*Texture.*—Upper side, leathery.
*Edge.*—Serrated.
*Serration.*—Single, small.
*Petiole.*—Rachis-Color, green. Upper side has small prickles along edge; underside, prickles.
*Stipules.*—Long, bearded.

*Disease resistance.*—Resistant to mildew under normal growing conditions at Irvine, Calif.
Wood:
*New wood.*—Color, light green. Bark, smooth.
*Old wood.*—Color, green. Bark, smooth.
Prickles:
*Quantity.*—On main stalks from base, ordinary. On laterals from stalk, ordinary.
*Form.*—Oval base, long.
*Color when young.*—Brown.
*Position.*—Irregular.
Small prickles:
*Quantity.*—None on main stalks or laterals.
*Color.*—None.

I claim:

1. A new and distinct variety of rose plant of the floribunda class, substantially as herein shown and described, characterized particularly as to novelty by the unique combination of yellow color, without reddish tints, large receptacles, red purple styles, upright bush and strong fragrance.

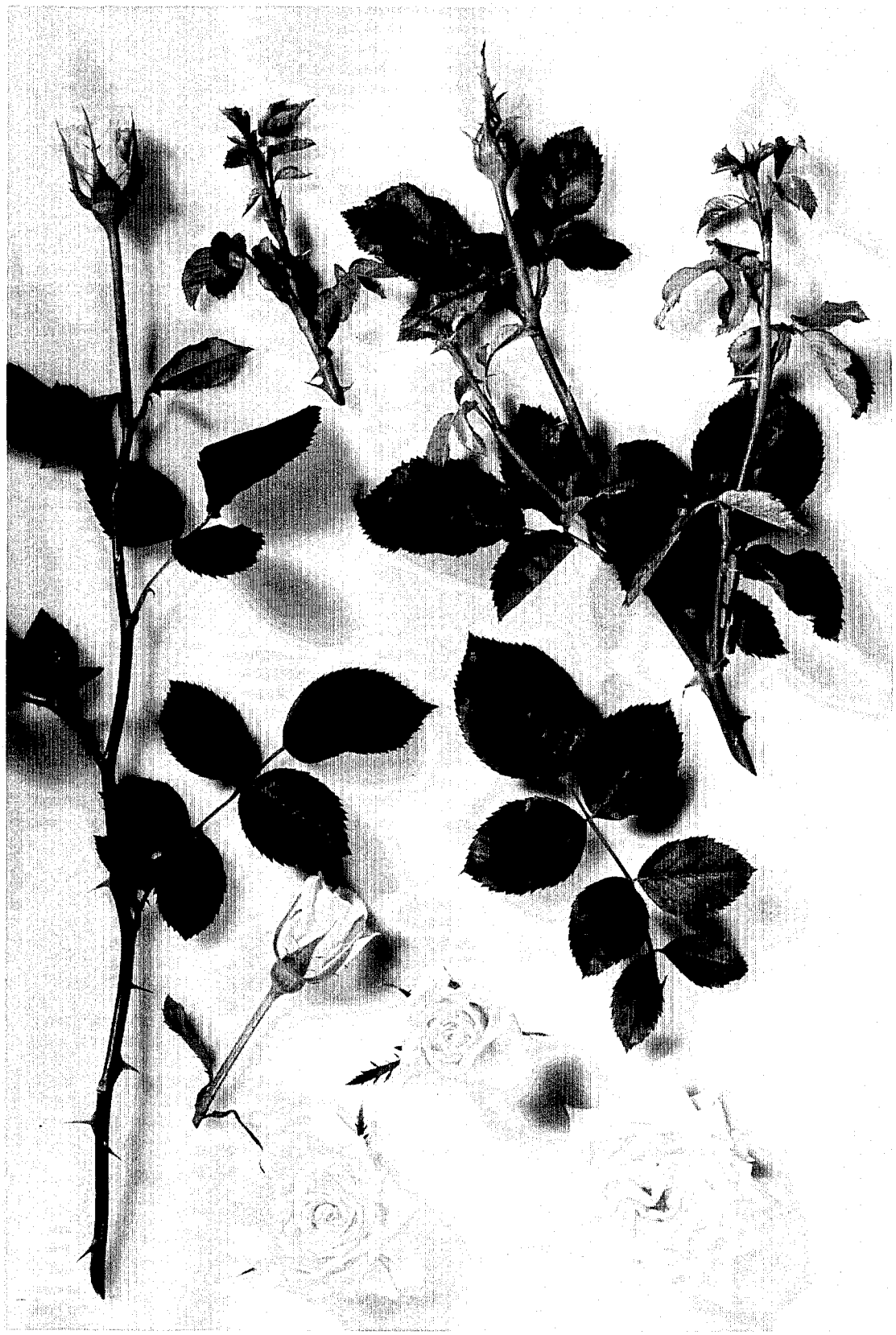

* * * * *